United States Patent [19]

Goldwasser et al.

[11] Patent Number: 4,593,110

[45] Date of Patent: Jun. 3, 1986

[54] PREPARATION OF 1,3-DIOXA-5,5,6,6,7,7-HEXAFLUOROCYCLOOCTANE

[75] Inventors: Judah M. Goldwasser; Horst G. Adolph; Cynthia L. Ebner, all of Silver Spring, Md.

[73] Assignee: The United States of America as represented by the Secretary of the Navy, Washington, D.C.

[21] Appl. No.: 752,704

[22] Filed: Jul. 8, 1985

[51] Int. Cl.$^4$ ........................................... C07D 321/12
[52] U.S. Cl. .................................................... 549/347
[58] Field of Search ........................................ 549/347

[56] References Cited

U.S. PATENT DOCUMENTS 3,419,531 12/1968 Trischler .............................. 549/347

FOREIGN PATENT DOCUMENTS 1294657 11/1972 United Kingdom ................ 549/347

OTHER PUBLICATIONS

K. G. Shipp et al., Jour. Org. Chem., vol. 31, (1966) pp. 853–856.

*Primary Examiner*—Norma S. Milestone
*Attorney, Agent, or Firm*—Robert F. Beers; Kenneth E. Walden; Roger D. Johnson

[57] ABSTRACT

One mole of 2,2,3,3,4,4-hexafluoropentane-1,5-diol is reacted with one mole of formaldehyde in the presence of an excess of trifluoromethanesulfonic acid to produce 1,3-dioxa-5,5,6,6,7,7-hexafluorocyclooctane.

4 Claims, No Drawings

PREPARATION OF 1,3-DIOXA-5,5,6,6,7,7-HEXAFLUOROCYCLOOCTANE

BACKGROUND OF THE INVENTION

This invention relates generally to organic synthesis and more particularly to the formation of cyclic formals from negatively substituted diols and formaldehyde.

In general, the formation of acetals and formals has been accomplished through the use of acid catalysts and often times with the addition of dehydrating agents. This is done in order to remove the water formed and shift the reaction equilibrium towards continued acetal formation. Several different dehydrating agents have so been employed. Alternatively, this may be accomplished by removing the water produced by azeotropic distillation (see H. M. Flowers in *The Chemistry of the Hydroxyl Group*, S. Patai Ed., J. Wiley and Sons Ltd., London (1971), pg 1028).

It was found in cases where the alcohol contained electron withdrawing substituents (as with the object compound of this invention) that acetal or formal formation would proceed only under severe reaction conditions. Usually, strong acids such as concentrated sulphuric acid are used. In those instances, degree of conversion to acetal was sensitive to acid concentration, reagent concentration, and reaction temperature. As a consequence, reaction conditions must be optimized and stringently controlled (see K. G. Shipp and M. E. Hill, J. Org. Chem., 31, 853 (1966)).

Alternatively, successful formation of acetals and formals has been accomplished by means of reaction of the alkoxide with a geminal dihalide. However, product yields obtained using this procedure were generally lower than those attainable using the acid catalysis method.

SUMMARY OF THE INVENTION

Accordingly an object of this invention is to provide a new method of preparing 1,3-dioxa-5,5,6,6,7,7-hexafluorocyclooctane.

Another object of this invention is to provide a simpler, more easily controlled method of preparing 1,3-dioxa-5,5,6,6,7,7-hexafluorocyclooctane.

A further object of this invention is to provide a new process which produces 1,3-dioxa-5,5,6,6,7,7-hexafluorocyclooctane in a much higher yield.

These and other objectives of this invention are achieved by reacting 2,2,3,3,4,4-hexafluoropentane-1,5-diol with formaldehyde in the presence of an excess of trifluoromethanesulfonic acid, $F_3CSO_2OH$ to produce 1,3-dioxa-5,5,6,6,7,7-hexafluorocyclooctane.

DETAILED DESCRIPTION OF THE PREFERRED EMBODIMENT

This invention is based upon the discovery that 1,3-dioxa-5,5,6,6,7,7-hexafluorocyclooctane can be produced by the reaction of formaldehyde and 2,2,3,3,4,4-hexafluoropentane-1,5-diol in the presence of trifluoromethanesulfonic acid, $F_3CSO_2OH$, in yields of more than 80 percent. One mole of formaldehyde, $CH_2O$, and one mole of the diol, $HOCH_2CF_2CF_2CF_2CH_2OH$ react to form the product

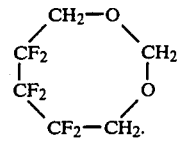

An excess, preferably a large excess, of the catalyst trifluoromethanesulfonic acid is used so that water generated by the reaction is taken up so as not to inhibit the reaction. Preferably the weight ratio of trifluoromethanesulfonic acid to 2,2,3,3,4,4-hexafluoropentane-1,5-diol is from about 3:1 to about 4:1 with about 3.5:1 being more preferred.

The formaldehyde may be added as formaldehyde (a gas), paraformaldehyde, (the polymer of formaldehyde), or trioxane (the trimer of formaldehyde). Preferably, paraformaldehyde is used because trioxane is (more) difficult to remove from the reaction mixture.

Although the reaction can be run without a solvent, the yield is increased by the use of a dry chlorohydrocarbon solvent. Preferred solvents are methylene chloride, chloroform, 1,2-dichloroethane, 1,1,2-trichloroethane, 1,1,1-trichloroethane, or mixtures thereof, with methylene chloride being the most preferred solvent. As stated above water is detrimental to the reaction. Therefore, the solvent should be dry as this will reduce the amount of dehydrating agent (acid) needed.

When the preferred paraformaldehyde (polymer) is used, it is suspended in the hydrocarbon solvent. But when trioxane (trimer) is used, it is dissolved in the hydrocarbon solvent prior to addition of the diol. The trifluoromethanesulfonic is added to the mixture of diol, formaldehyde (monomer, polymer, or trimer), and hydrocarbon solvent at a moderate rate with stirring so as to avoid overheating or splattering of the reaction mixture.

The reaction can be run at ambient temperature ($\sim 20°$ C.) and pressure as illustrated by the examples. Temperature control is a non-critical parameter.

The product 1,3-dioxa-5,5,6,6,7,7-hexafluorocyclooctane is isolated and purified by conventional means as illustrated by the examples.

The general nature of the invention having been set forth, the following examples are presented as a specific illustrations thereof. It will be understood that the invention is not limited to these examples but is susceptible to various modifications that will be recognized by one of ordinary skill in the art.

EXAMPLE 1

Using Trioxane 100 g (0.47 mole) of 2,2,3,3,4,4-hexafluoropentane-1,5-diol were added to a solution of 20 g (0.67 mole) of trioxane (trimer of formaldehyde) dissolved in dry $CH_2Cl_2$. While stirring, 40 ml of trifluoromethanesulfonic acid were added at a moderate rate. The reaction mixture was then stirred at room temperature ($\sim 20°$ C.) for 90 minutes, after which time 100 ml of water were added to dilute the trifluoromethanesulfonic acid with cooling. The $CH_2Cl_2$ solution was washed with a dilute basic aqueous hydrogen peroxide solution (3% $H_2O_2$, 10% KOH) and brine, dried, and filtered. Removal of the $CH_2Cl_2$ by rotary evaporation yielded a quantitative amount of the crude product as a viscous oil. Distillation of the product gave a pre-cut (b.p. 40°–165° C., mostly cyclic formal) and pure 1,3-dioxa-5,5,6,6,7,7-hexafluorocyclooctane (b.p. 165°–167° C., m p. 24°–25° C., density $1.584^{22}$) in 83% (88 g) yield. A high boiling residue (also mostly cyclic formal) remained.

EXAMPLE 2

Using Paraformaldehyde

To a mixture of 318 g (1.5 mol) of 2,2,3,3,4,4-hexafluoropentane-1,5-diol and 48 g (1.6 mol) of paraformaldehyde and 1200 ml of dry $CH_2Cl_2$ were added at a moderate rate with stirring 127 ml (1.44 mol) of triflic acid (trifluoromethanesulfonic acid). The reaction mixture was then stirred at room temperature (~20° C.) for 120 minutes after which time 800 ml of ice water were added to dilute the triflic acid. The phases were separated, the aqueous phase washed once with 200 ml of $CH_2Cl_2$ and the $CH_2Cl_2$ fractions were combined. The $CH_2Cl_2$ solution was then washed twice with 500 ml of 5% KOH, dried and filtered. Removal of the $CH_2Cl_2$ by distillation yielded a quantitative amount of the crude product as a vicous oil. Distillation of the product in vacuo (12 mm, 65° C.) yielded 86% (290 g) of pure 1,3-dioxa-5,5,6,6,7,7-hexafluorocyclooctane.

Obviously many modifications and variations of this invention are possible in light of the above teachings. It is therefore to be understood that within the scope of the appended claims the invention may be practiced otherwise than as specifically described.

What is claimed is:

1. A process for preparing 1,3-dioxa-5,5,6,6,7,7-hexafluorocyclooctane comprising the steps of
   (1) reacting one mole of 2,2,3,3,4,4-hexafluoropentane-1,5-diol with one mole of formaldehyde in the presence of an excess of trifluoromethanesulfonic acid; and
   (2) isolating the product 1,3-dioxa-5,5,6,6,7,7-hexafluorocyclooctane.

2. The process of claim 1 wherein the weight ratio of trifluoromethanesulfonic acid to 2,2,3,3,4,4-hexafluoropentane-1,5-diol is from about 3:1 to about 4:1.

3. The process of claim 1 wherein the reaction is run in a solvent selected from the group consisting of methylene chloride, chloroform, 1,2-dichloroethane, 1,1,2-trichloroethane, 1,1,1-trichloroethane, or mixtures thereof.

4. The process of claim 3 wherein the solvent is methylene chloride.

* * * * *